United States Patent [19]

Schorlemmer et al.

[11] Patent Number: 4,578,399

[45] Date of Patent: Mar. 25, 1986

[54] USE OF THE DITERPENE DERIVATIVE FORSKOLIN FOR IMMUNOSTIMULATION

[75] Inventors: Hans-Ulrich Schorlemmer, Weimar; Gerhard Dickneite; Hans-Harald Sedlacek, both of Marburg, all of Fed. Rep. of Germany; Noel J. de Souza; Alihussein N. Dohadwalla, both of Bombay, India

[73] Assignee: Hoechst Aktiengesellschaft, Frankfurt, Fed. Rep. of Germany

[21] Appl. No.: 603,347

[22] Filed: Apr. 24, 1984

[30] Foreign Application Priority Data

Apr. 26, 1983 [DE] Fed. Rep. of Germany ....... 3314999

[51] Int. Cl.$^4$ .............................................. A61K 31/35
[52] U.S. Cl. ................................... 514/455; 514/885
[58] Field of Search ................ 424/283; 514/455, 885

[56] References Cited

U.S. PATENT DOCUMENTS

| | | | |
|---|---|---|---|
| 4,134,986 | 1/1979 | Bajwa et al. | 424/283 |
| 4,198,426 | 4/1980 | Philip et al. | 424/283 |
| 4,299,916 | 11/1981 | Litman et al. | 435/6 |
| 4,376,821 | 3/1983 | Braude | 435/68 |
| 4,376,822 | 3/1983 | Braude | 435/68 |
| 4,391,904 | 7/1983 | Litman et al. | 435/7 |
| 4,460,685 | 7/1984 | Vilcek et al. | 424/85 |
| 4,476,140 | 10/1984 | Sears et al. | 424/283 |

OTHER PUBLICATIONS

Chem. Abst. 91, 21671m (1979)—DeSouza.
Chem. Abst. 96 192749(c) (1982)—Koch.
Chem. Abst. 98 191060(a) (1983)—Seamon et al.
Chem. Abst. 99 32604(lc) (1983)—DeSouza et al.

*Primary Examiner*—Douglas W. Robinson
*Attorney, Agent, or Firm*—Finnegan, Henderson, Farabow, Garrett & Dunner

[57] ABSTRACT

The possibility of using the diterpene derivative forskolin (1α, 6β, 9α-trihydroxy-7β-acetoxy-8,13-epoxy-14-labden-11-one) to increase the immunological responsiveness of mammals is described.

4 Claims, No Drawings

USE OF THE DITERPENE DERIVATIVE FORSKOLIN FOR IMMUNOSTIMULATION

The invention relates to the use of the pharmacologically active diterpene derivative forskolin to stimulate the immunological responsiveness in mammals.

Forskolin is described in German Offenlegungsschrift No. 2,557,784, and the following structure has been reported for it:

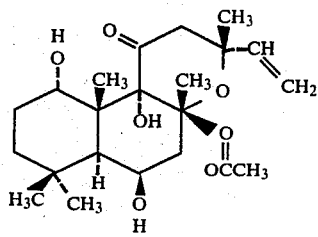

($1\alpha,6\beta,9\alpha$-trihydroxy-$7\beta$-acetoxy-8,13-epoxy-14-labden-11-one).

Forskolin was isolated from *Coleus forskohlii* and has positive inotropic and hypotensive effects. It activates membrane-bound adenylate cyclase in all the mammalian tissues hitherto investigated, and this leads to an increase in the cellular level of cAMP.

It is known that the defense mechanisms of the organism, which are referred to in short as the humoral immunity and the cellular immunity, cooperate to eliminate foreign bodies which may be injurious, principally microorganisms or neoplastic cells.

Immunological investigations have shown that there are connections between the reduction in immunological activity which occurs naturally or is provoked by external factors and the increase in the risk of infection or tumors. Moreover, other diseases occur due to changes in the functioning of the immune system, such as, for example, autoimmune diseases or disorders induced by antigen-antibody complexes, intoxication, septicemia and the like. For this reason, there is a search for immunostimulants, ie. substances which are capable of changing the immunological activity of the recipient, preferably raising it. Examples which have been tested in respect of their stimulation of immunity, are BCG and *C. parvum*, also the extracts of *M. tuberculosis* and the brucellae.

However, in the concentrations which are used, these substances produce marked side effects, such as, for example, local granulomas in varying extents. The lack of knowledge of the exact nature of the substances makes it difficult to carry out a systematic investigation with good reproducibility of the clinical results. In this connection, the new generation of immunostimulants containing chemically exactly defined substances and having low toxicity, such as, for example, bestatin, is an improvement.

It has now been found, surprisingly, that forskolin, at a concentration of less than 20 mg/kg body weight, stimulates the immune response in warm-blooded mammals without at the same time exhibiting toxic side effects, and is thus suitable for the treatment of disorders of the immune system. This compound increases the production of antibodies and strengthens cellular immunity, and thus permits the restitution of immunological activity to those patients whose immunological defenses have been diminished in a natural way or by some type of provocation.

The invention relates to the use of forskolin as an immunopotentiator.

The effective immunostimulant amount on parenteral administration is in the range from 2.5 to 20 mg/kg body weight.

Suitable for parenteral, in particular intravenous, administration are solutions or suspensions of the active compound in a pharmaceutically tolerated vehicle, preferable vegetable oil, such as, for example, peanut oil or sesame oil, and alcoholic solutions of the active compound, for example in ethanol, propanediol or glycerol, or in mixtures of the abovementioned solvents.

The compound used according to the invention has, in the concentration ranges effective for this, only low toxicity, and it does not lead to the local formation of granulomas.

The action of the compound on the immune response in the mouse and its immunostimulant activity in various standard in vitro and in vivo test methods, which are known to be used for the assessment of immunostimulants, are illustrated by way of example below.

EXAMPLE 1

Effect of the substance on the antibody response to killed *Escherichia coli* organisms In each instance, $10^8$ heat-killed *E.coli* bacteria per animal were administered intravenously to groups of 5 female NMRI mice weighing 18–20 g. At the same time, physiological saline was administered intravenously to one of these groups of mice as a control. At the same time but separately, other groups received, by the intravenous route, the test substance in various concentrations in physiological saline, the doses increasing stepwise from 2.5 mg/kg to 5 mg/kg, 10 mg/kg and 20 mg/kg.

20 days after injection of the antigen and the various concentrations of the compound forskolin, blood was taken from the retroorbital venous plexus of the mice, and the antibodies to *E.coli* in the serum obtained from this were determined. The antibodies (IgG) were determined using the ELISA technique which is known to the expert, the antigen used being homologous lipopolysaccharide from *E.coli*. The values for the extinction measured in a photometer are a measure of the amount of antibody formed. The results are compiled in Table 1 below.

TABLE 1

Effect of forskolin on the antibody response on immunization of mice with killed *Escherichia coli* organisms

| 1 × Administration i.v. on day 0 | Antibody response (mE$_{492\ nm}$ - ELISA assay) |
| --- | --- |
| PBS | 1151 ± 311 |
| Forskolin 2.5 mg/kg | 1382 ± 324 |
| Forskolin 5 mg/kg | 1692 ± 192* |
| Forskolin 10 mg/kg | 1551 ± 332** |

Statistical significance (student's t test:
*$p < 0.01$;
**$p < 0.05$)

It can be seen from Table 1 that, in the mouse model investigated, the substance leads to a dose-dependent stimulation of the antibody response. A maximum immunostimulant effect of the compound is achieved at a dose of 5 mg/kg.

EXAMPLE 2

Effect of forskolin on the cellular immune response to sheep erythrocytes

In this example, mice were treated in a manner analogous to that described in Example 1, with the difference that the mice received intravenous injections of either $10^6$ or $10^9$ red blood cells from sheep per animal. In immunology, sheep erythrocytes are regarded as a standard test substance (antigen) for the detection of the cellular and humoral immune responses. At the same time, the substance according to the invention was administered intravenously in the concentrations 2.5 mg kg, 5 mg/kg, 10 mg/kg and 20 mg/kg in physiological saline. After 5 days, in each instance $2 \times 10^8$ sheep erythrocytes were injected into the footpads of all the mice, and the swelling of the foot 24 hours later was measured. The swelling of the foot is induced by a skin reaction of the delayed type (delayed-type hypersensitivity, DTH) and is, as is known to the expert, a measure of the cellular immune response (Collins, F. M. and Mackaness, G. B., J. Immunol. (1968), 101, 830–845). The results compiled in Table 2 illustrate that administration of forskolin increases the cellular immune response after immunization both with $10^6$ and with $10^9$ sheep erythrocytes. In this design of experiment, the maximum stimulation is again observed on administration of 5 mg/kg substance.

TABLE 2

Immunization of mice with sheep erythrocytes - effect of forskolin on the cellular immune response (DTH response)

| 1 × i.v. administration of | % swelling of the foot with $10^6$ erythrocytes |
|---|---|
| PBS | 16.0 |
| Forskolin 2.5 mg/kg | 18.6 |
| Forskolin 5 mg/kg | 21.5 |
| Forskolin 10 mg/kg | 17.1 |
| Forskolin 20 mg/kg | 23.2 |

EXAMPLE 3

The effect of forskolin on the stimulation of the nonspecific immune activation of mononuclear phagocytes In this instance, the effect of the compound used according to the invention on the stimulation of peritoneal macrophages in 6–8 week-old NMRI mice was investigated. Female mice received by parenteral routes (intravenous and intraperitoneal) the test substance at a dose of 2.5 mg/kg, 5 mg/kg, 10 mg/kg and 20 mg/kg. Buffered saline was administered to the control group. The mice were sacrificed 3 days after the injections, and the peritoneal macrophages in the animals were examined for their state of activation. The secretion of the lysosomal enzymes ($\beta$-glucuronidase, $\beta$-galactosidase, N-acetyl-$\beta$-D-glucosaminidase) was determined as one measure of the macrophage activation. On the other hand, it was possible, using the RIA technique (as is known to the expert), also to investigate the synthesis of prostaglandins $E_2$ and $F_2\alpha$ in the same cultures of macrophages. The level of oxidative metabolism in macrophages is taken to be another measure of their state of activation. This activity is measured with the assistance of the biolumate by determining the chemoluminescence.

For this purpose, cultivation at 5% $CO_2$ and 37° C. was carried out either with $3 \times 10^6$ macrophages in 1 ml TC199 culture medium in 30 mm diameter Petri dishes or $10^6$ macrophages in 100 $\mu$l medium in round-bottomed polyethylene tubes (to determine the chemoluminescence). After incubation for one hour, the cultures were rinsed to remove floating cells. The chemoluminescence (tube culture) was then determined directly, while the Petri dishes underwent renewed incubation at 37° C. for 24 hours, and then the enzyme and prostaglandin activities in the cultures were determined. The results obtained are shown below.

TABLE 3

Effect of forskolin on macrophage activity (chemoluminescence in RLU/15 minutes*)

| 1 × administration of | intraperitoneal | intravenous |
|---|---|---|
| PBS | 1855 ± 59 | 1263 ± 37 |
| Forskolin 2.5 mg/kg | 6529 ± 74 | 3351 ± 42 |
| Forskolin 5 mg/kg | 17134 ± 142 | 10476 ± 98 |
| Forskolin 10 mg/kg | 24199 ± 295 | 18871 ± 211 |
| Forskolin 20 mg/kg | 38421 ± 232 | 26029 ± 145 |

*RLU = relative light units

Parenteral treatment of NMRI mice with forskolin leads to an immunity-stimulating effect. The oxidative metabolism in macrophages, with the generation of oxygen radicals and the measureable light associated with this, is markedly increased. There is a dose-dependent increase in macrophage activity at doses of 2.5 mg/kg and above.

It can be seen from Table 4 that macrophages from control mice release only small amounts of lysosomal enzymes ($\beta$-glucuronidase, $\beta$-galactosidase, N-acetyl-$\beta$-D-glucosaminidase) into the culture supernatant. Mononuclear phagocytes from mice which were treated parenterally with the compound for 72 hours secrete markedly more of the abovementioned acid hydrolases ($\beta$-Glu, $\beta$-Gal and N-acetyl-Glu), and thus exhibit a dose-activity curve which for all measured enzymes demonstrates superiority over the controls. It is evident that forskolin has a stimulant effect on macrophage activity and contributes to increasing the release of enzymes.

TABLE 4

Effect of the test substance on the release of lysosomal hydrolase enzymes from mouse peritoneal macrophages

| 1 × i.p./i.v. administration | $\beta$-Glu mU/ml | $\beta$-Gal mU/ml | N—Acetyl-Glu mU/ml |
|---|---|---|---|
| PBS | 817/709 | 5866/4429 | 5426/3120 |
| Forskolin 2.5 mg/kg | 1088/924 | 9532/7537 | 748/4842 |
| Forskolin 5 mg/kg | 1305/1181 | 11418/9250 | 9076/5665 |
| Forskolin 10 mg/kg | 1487/1363 | 12358/10812 | 12479/7081 |
| Forskolin 20 mg/kg | 1669/1575 | 13867/12228 | 15812/9146 |

The results in Table 5 illustrate the effect of forskolin on prostaglandin production. This effect was measured by the amount (pg/ml) of synthesized prostaglandins $E_2$ and $F_2\alpha$ in the culture supernatant. Depending on the treatment dose, intravenous administration of the test substance to NMRI mice significantly increased the synthesis of prostaglandins by peritoneal macrophages.

TABLE 5

The effect of forskolin on prostaglandin production by mouse macrophages

| 1 × i.v. administration of | $PGE_2$ (pg/ml) | $PGF_{2\alpha}$ (pg/ml) |
|---|---|---|
| PBS | 724 | 598 |
| Forskolin 2.5 mg/kg | 4,356 | 2,644 |
| Forskolin 5 mg/kg | 7,082 | 3,782 |

TABLE 5-continued

The effect of forskolin on prostaglandin production by mouse macrophages

| 1 × i.v. administration of | PGE$_2$ (pg/ml) | PGF$_{2\alpha}$ (pg/ml) |
|---|---|---|
| Forskolin 10 mg/kg | 9,146 | 4,258 |
| Forskolin 20 mg/kg | 11,498 | 5,163 |

The results in Tables 3, 4 and 5 show clearly that the compound forskolin proved, at the various doses which were taken into consideration, to be effective for increasing the immunological potential to stimulate macrophage activity, and thus it led to stimulation of the non-specific immunity.

EXAMPLE 4

Kinetics of appearance of activated macrophages in mice treated with forskolin

In this example, mice were treated with 10 mg/kg of test substance in analogy to the manner described in Example 3. The mice were sacrificed on days 3, 4, 5, 6, 10, 11, 12 and 13 after injection, and the peritoneal macrophages in the animals were tested for their enzyme activity.

The results are compiled in Table 6.

TABLE 6

Kinetics of activated mouse peritoneal macrophages on treatment with forskolin. Determination of the % release of $\beta$-glucuronidase

| Days of enzyme determination ($\beta$-Glu) | i.v. administration | |
|---|---|---|
| | PBS | Forskolin (20 mg/kg) |
| 3 | 8.4 ± 0.7% | 21.3 ± 1.6% |
| 4 | 9.7 ± 1.2% | 28.9 ± 1.3% |
| 5 | 9.2 ± 0.5% | 37.4 ± 1.5% |
| 6 | 10.6 ± 1.4% | 46.8 ± 1.9% |
| 10 | 9.5 ± 0.8% | 53.6 ± 2.2% |

TABLE 6-continued

Kinetics of activated mouse peritoneal macrophages on treatment with forskolin. Determination of the % release of $\beta$-glucuronidase

| Days of enzyme determination ($\beta$-Glu) | i.v. administration | |
|---|---|---|
| | PBS | Forskolin (20 mg/kg) |
| 11 | 11.3 ± 1.1% | 41.7 ± 1.6% |
| 12 | 10.9 ± 0.9% | 32.4 ± 1.5% |
| 13 | 9.8 ± 1.0% | 26.8 ± 1.1% |

The appearance of activated macrophages (in this instance determined by the % release of the lysosomal enzyme $\beta$-glucuronidase) is quite rapid. The macrophages are activated after only 3 days, and their activity continues to increase to reach an optimum on days 6–10, then their activity decreases again with increasing time after the injection of forskolin. In contrast to this, macrophages from control animals (PBS treatment) show no increased enzyme activity at any time.

It can be seen from these results in Table 6 that, on intravenous administration of 10 mg/kg forskolin to mice, the non-specific immunity (macrophage activity) is stimulated after only 3 days; however, the optimum stimulation is not reached until after about 10 days.

Thus, in summary it can be stated that, in various standard in vitro and in vivo test methods which are generally employed to assess immunostimulants, forskolin is capable of increasing the immunological activity of the recipient. Thus, forskolin is also capable of activating the defense mechanisms of the organism, and can contribute to reducing the risks of infection and tumors.

We claim:

1. A method of stimulating the immune system of a mammal which comprises parenterally administering to said mammal a therapeutically effective amount of forskolin to provide immunostimulation.

2. The method of claim 1 wherein said forskolin is in a pharmaceutically tolerated carrier.

3. The method of claim 1 wherein said parenteral administration further comprises intravenous administration.

4. The method of claim 1 wherein said amount ranges from 2.5 to 20 mg of forskolin per kg of body weight of said subject.

* * * * *